United States Patent [19]

Okada et al.

[11] Patent Number: 5,125,741
[45] Date of Patent: Jun. 30, 1992

[54] METHOD AND APPARATUS FOR INSPECTING SURFACE CONDITIONS

[75] Inventors: Saburo Okada; Tetsuhiro Sumimoto; Masaaki Imade; Hidekazu Miyauchi, all of Kure, Japan

[73] Assignee: Agency of Industrial Science & Technology, Tokyo, Japan

[21] Appl. No.: 669,998

[22] Filed: Mar. 15, 1991

[30] Foreign Application Priority Data

Mar. 16, 1990 [JP] Japan .................................... 2-67839

[51] Int. Cl.⁵ ............................................ G01N 21/88
[52] U.S. Cl. ................................... 356/237; 356/371; 356/446
[58] Field of Search ............... 356/237, 429, 446, 371, 356/431, 394, 376, 430

[56] References Cited

U.S. PATENT DOCUMENTS

| | | | |
|---|---|---|---|
| 4,632,546 | 12/1986 | Sick et al. | 356/237 |
| 4,741,621 | 5/1988 | Taft et al. | 356/237 |
| 4,866,288 | 9/1989 | Weber | 356/131 |

FOREIGN PATENT DOCUMENTS

| | | | |
|---|---|---|---|
| 163952 | 7/1987 | Japan | 356/237 |
| 235549 | 10/1987 | Japan | 356/237 |
| 47641 | 2/1988 | Japan | 356/237 |

*Primary Examiner*—Richard A. Rosenberger
*Attorney, Agent, or Firm*—Oblon, Spivak, McClelland, Maier & Neustadt

[57] ABSTRACT

This invention concerns inspection of surface conditions to detect locations, sizes and nature of flaws, defects or stains not only on a flat surface but also on an undulating or stepped surface, and includes the steps of: scanning an inspecting surface of a specimen with a spot-like laser beam projected obliquely from a light source; detecting the height of the inspecting surface from a reflected image of the scanning light picked up by a TV camera located above the inspecting surface, to maintain the inspecting surface at a constant height; converging reflected and diffracted light from the inspecting surface toward a photo-detector having measuring points at the point of convergence and at a number of positions along a concentric circle around the point of convergence; measuring the energy of the reflected and diffracted light by photoelectric transducers connected to the respective measuring points; and displaying locations, sizes and nature of surface flaws, defects and stains of the specimen on a monitor, with combined use of information provided by the picture image of the TV camera as to variations in surface level and cracks on the inspecting surface.

7 Claims, 3 Drawing Sheets 5,125,741

METHOD AND APPARATUS FOR INSPECTING SURFACE CONDITIONS

BACKGROUND OF THE INVENTION

1. Field of the invention

This invention relates to a method and an apparatus for high-speed and high-precision inspection of surface conditions of various articles having not only flat surfaces of metal or glass sheets or the like but also undulating or stepped surfaces on components of machines and electrical appliances and instruments, detecting locations, sizes and nature of flaws or defects if any

2. Description of the Prior Art

The inspection of flaws or defects on the surfaces of materials and products is essential in various industrial fields, for example, in the fields of automobiles, electrical appliances and so forth. In the surface inspection, in addition to the locations and sizes of surface flaws or defects, it is normally required to detect the kind or nature of surface flaw or defects To meet such a requirement, it has been the usual practice for the conventional surface inspection machines to resort to the so-called flying spot method using a laser beam in a light-spot scanning system. In the flying spot method, a light beam from a laser source is spotted on and scanned along a surface of specimen, inspecting the surface condition by means of a detection system which receives reflected and diffracted light from the surface under inspection. Existing detection systems are largely classified into multiple photocell type, diffraction pattern projection type, mirror convergence type and diffuser convergence type. In any case, the inspection is restricted to plano surfaces such as surfaces of flat glass sheets, metal sheets and film-like materials, and not applicable to articles which contain ups and downs or undulations on the surfaces thereof More specifically, in case of a specimen with stepped surface portions, the surface level for inspection varies from one position to another, so that an obliquely incident scanning light beam is reflected at different positions (levels) on the surface of a specimen, the reflected light often failing to enter the detection system to form an image therein.

Even in a case where the reflected light is anyhow led into the optical detection system, it is difficult to detect an accurate diffraction pattern of reflected and diffracted light from a specimen surface, which is essential for accurate judgement of the nature of a surface flaw or defect.

FIG. 4 shows by way of example the construction of a conventional surface inspection apparatus based on the multiple photocell method, in which a light beam from a laser generator 31 is projected toward a vibrating mirror 33 through a collimator lens 32, thereby changing the direction of the irradiating light beam at high speed to scan the surface of a specimen 34 from an oblique direction. On the part of the photometric detection system, a couple of photocells 35 and 36 are provided side by side, one for reflected light and the other for diffracted light, the output of these photocells being sent to an analogue arithmetic unit 39 through amplifiers 37 and 38, respectively.

The photometric detection system of this sort is capable of determining the amount of diffracted light but due to its construction incapable of determining the direction of the diffraction pattern which is necessary for judging the nature of a surface flaw.

Further, as shown in FIG. 5, in the diffraction pattern projection method, a light beam from a laser beam generator 41 is projected on a specimen 42, and the image of a diffraction pattern which appears on a screen 43 is taken by a camera or other suitable image pick-up means for judgement of the nature of surface flaws. In this case, however, the measurement gives information of a particular point, and the specimen or optical system has to be moved for two-dimensional scanning in order to obtain information on a certain area of a surface, requiring a great deal of time for inspection.

Thus, the conventional technologies in surface defect detection do not permit three-dimensional measurement of a specimen simultaneously with the detection of a diffraction pattern, making it difficult to judge the nature of flows or defects on the surface of specimen accurately at high speed especially in a case where the specimen has an undulating or stepped surface.

SUMMARY OF THE INVENTION

It is an object of the present invention to provide a method and an apparatus for inspection of surface conditions, which can overcome the above-mentioned problems, that is to say, which can accurately detect and measure flaws, defects, cracks or stains on a surface even when the specimen has an undulating or stepped surface.

It is another object of the present invention to provide a method and an apparatus for inspection of surface conditions, which can detect the locations and sizes of flaws, defects and stains on a surface.

It is still another object of the invention to provide a method and an apparatus for inspection of surface conditions, employing a TV camera and photoelectric transducers in a photo-detection system to maintain a surface under inspection at a constant height during measurement even in case of a specimen which contains undulations or stepped portions on its surface, thereby permitting to detect the nature of surface defects and flaws accurately in a reliable manner.

In accordance with the present invention, there is provided, for achieving the above-stated objectives, a method for inspection of surface conditions by scanning a surface of specimen with a spot-like light beam projected obliquely from a light source and detecting various defects on the surface of the specimen on the basis of optical data of diffracted light from the specimen surface, characterized in that the method comprises: detecting the height of the surface under inspection from a reflection image of the scanning light picked up by a TV camera located above the inspecting surface; controlling the vertical position of the specimen according to the output of the height detection in such a manner as to maintain the inspecting surface of the specimen at a constant height; converging reflected and diffracted light from the inspecting surface by means of a parabolic cylinder mirror toward a photo-detector having measuring points at the point of convergence and in a number of positions on and along a concentric circle around the point of convergence; measuring the energy of reflected and diffracted light by photoelectric transducers connected to the measuring points; and displaying locations, sizes and nature of surface flaws, defects and stains of the specimen, if any, on a monitor with combined use of information provided by the TV camera as to variations in surface level and cracks on the inspecting surface under inspection.

In accordance with the present invention, there is also provided an apparatus for inspection of surface conditions, essentially including in combination: a laser generator for projecting a laser beam for irradiation; a vibrating mirror adapted to change the direction of irradiation of the laser beam at high speed for scanning same in a direction perpendicular to the direction of transfer of the specimen; a first parabolic cylinder mirror for converting the scanning light from the vibrating mirror into a parallel beam and projecting same obliquely on the surface of the specimen; a TV camera located above the inspecting surface of the specimen; an image processing unit for detecting the height of the inspecting surface through analysis of the picture image picked up by the TV camera; a second parabolic cylinder mirror for converging the scanning laser light scattered from the inspecting surface; a photo-detector adapted to receive the reflected and diffracted light from the parabolic cylinder mirror at a number of measuring points located at the point of convergence and on a concentric circle around the point of convergence and to measure the energy level of the incident reflected and diffracted light by means of photoelectric transducers; a specimen mounting stage arranged to be controlled by the output of the image processing unit to maintain the inspecting surface of the specimen at a constant height; a slider for moving the stage in the direction of transfer of the specimen; a data processing unit adapted to judge locations, sizes and nature of surface flaws, defects and cracks, if any, according to information from the image processing unit and photo-detector; and a display for indicating the results of judgement of the data processing unit.

According to the above-described method and apparatus of the invention, a spot-like light beam is scanned by the use of a vibrating mirror in synchronism with video signal to permit simultaneous measurements by light diffraction method and light chopping method for inspection with the advantages of the two methods Namely, the three-dimensional shape of an inspecting surface is measured by the light chopping method, thereby automatically controlling the height of the specimen in such a manner as to maintain the position of beam irradiation at a constant height and thus converging the diffracted light at a predetermined point on the photo-detector to permit automatic inspection of various surfaces

BRIEF DESCRIPTION OF THE DRAWINGS

The above and other objects, features and advantages of the invention will become apparent from the following description and the appended claims, taken in conjunction with the accompanying drawings which show by way of example a preferred embodiment of the invention and in which:

DESCRIPTION OF PREFERRED EMBODIMENTS

Figure 1:
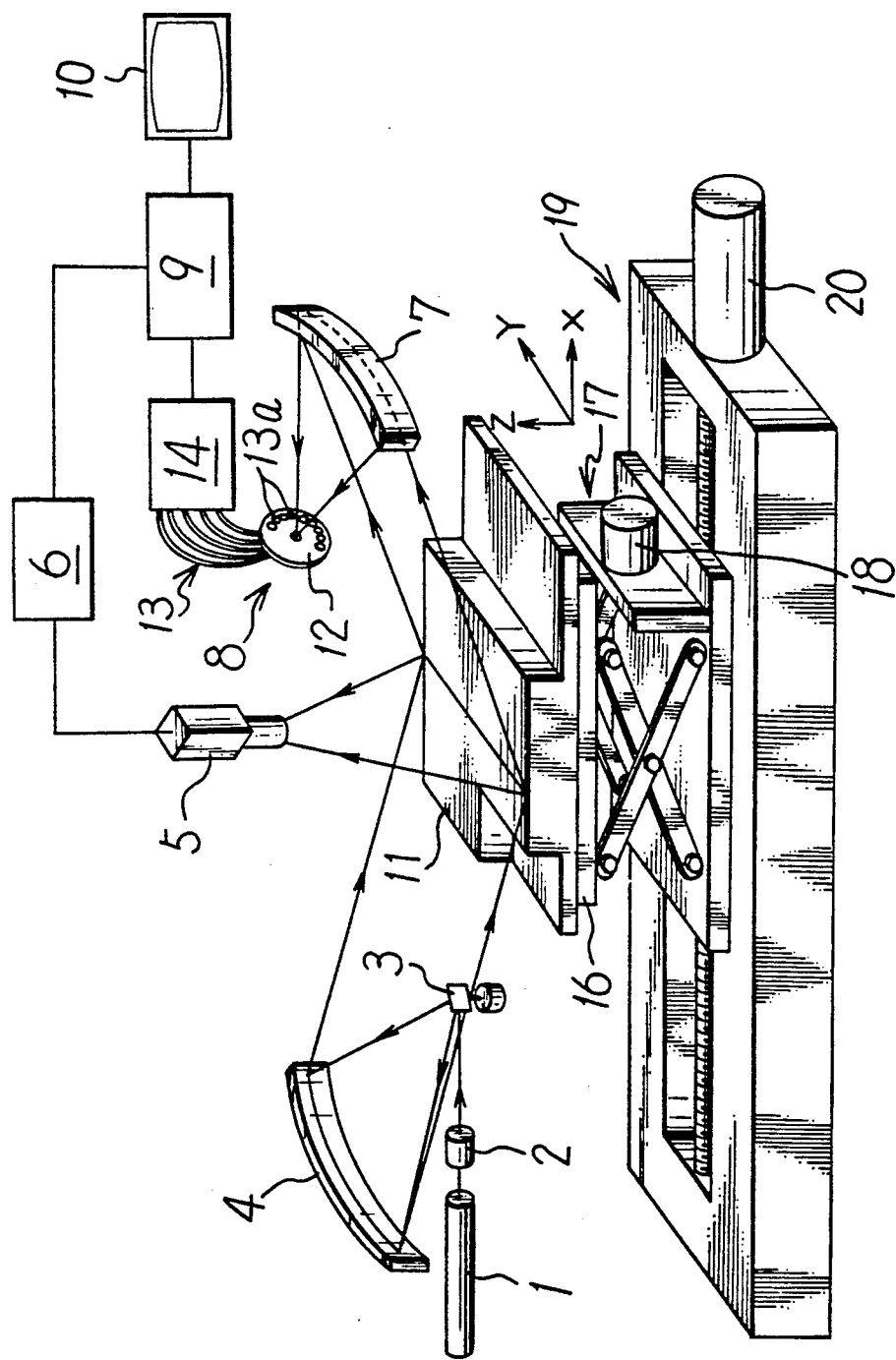
FIG. 1 is a schematic view of an apparatus employed for carrying out a method of inspection of surface conditions according to the invention.

Referring to FIG. 1, there is schematically shown an apparatus employed for carrying out the method of inspection of surface conditions according to the present invention.

The apparatus has a light projection system, which includes a laser generator 1 which serves as a light source for emitting a laser beam, a collimator lens 2 which adjusts the beam diameter, a vibrating mirror 3 which changes the direction of the beam at high speed for light-spot scanning obliquely in a direction (Y-direction) perpendicular to the direction of transfer of a specimen 11, and a parabolic cylinder mirror 4 which converts the scanning light from the vibrating mirror 3 into a parallel light beam.

On the light receiving side, the apparatus is provided with a photo-detection system including a TV camera located immediately above the surface of the specimen under inspection, an image processing unit 6 connected to the TV camera to analyze the picture image picked up by the camera, a parabolic cylinder mirror 7 for converging the scanning laser light reflected and scattered at various portions of the inspecting surface, a photo-detector member 8 for receiving reflected and diffracted light from the parabolic cylinder mirror 7, a data processing unit 9 arranged to judge the locations, sizes and nature of surface flaws, defects, cracks etc. on the basis of information received from the image processing unit 6 and photo-detector member 8, and a display 10 adapted to indicate the results of judgement of the data processing unit 9 according to the nature of surface flaws or defects.

Figure 2:
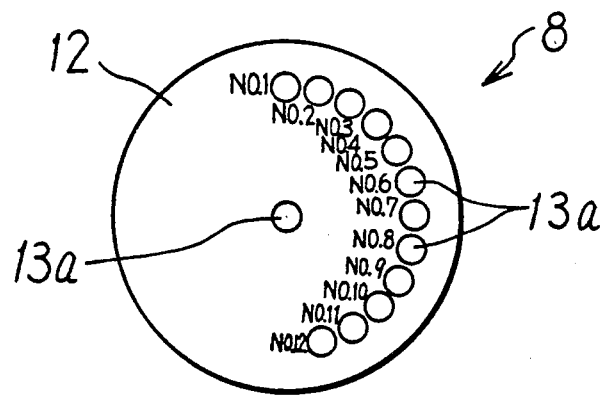
FIG. 2 is a schematic front view of a light receiving end of an optical fiber cable.

Shown in FIG. 2 is the arrangement of light receiving ends 13a of individual optical fiber filaments 13 on a light receiving surface 12 of the photo-detector member 8. On the light receiving surface 12, the light receiving ends 13a are located at the point of convergence and on a right half of a concentric circle around the point of convergence The other or proximal ends of the respective optical fiber filaments are connected to photoelectric transducers (photomultipliers) 14. The photoelectric transducers 14 need to be of low noise and high sensitivity in order to detect accurately even diffracted light of feeble levels.

Further, for maintaining the inspecting surface of the specimen 11 at a constant height, a stage 16 which mounts the specimen 11 is moved in Z-direction (in the vertical direction) by a slider 17 with a drive motor 18 and in X-direction by a slider 19 with a drive motor 20.

In operation, the above-described apparatus inspects the surface condition of the specimen 11 in the following manner.

The laser beam from the light source, that is, from the laser generator 1 is adjusted into a suitable beam diameter through the collimator lens 2 and deflected by the vibrating mirror which is located at the focal point of the mirror 4.

As the vibrating mirror 3 is put in vibration within a predetermined angle and at a predetermined frequency, the direction of the light beam reflected from the vibrating mirror 3 is sequentially changed along the parabolic cylinder mirror 4, the light beam being reflected from the mirror 4 in a parallel fashion and obliquely projected on the surface of the specimen under inspection to light-scan a specified area of the surface sequentially at a predetermined speed.

For automatic inspection of a surface which contains ups and downs or undulations, the TV camera 5 which is located immediately over the inspecting surface is adapted to pick up the image of the scanning laser light reflected from the inspecting surface, in synchronism with the light-spot scanning, detecting the position of reflection of the laser light at the image processing unit 6. Since the angle of incidence $\theta$ is known, the height H of a given surface portion of the specimen from a reference surface is expressed by the following equation.

$$H = d \tan \theta$$

where d is the amount of deviation from a reference position of the detected image of reflected laser light.

On the basis of the output of calculation of the height H from the reference surface by the image processing unit 6, the stage 16 which holds the specimen 11 is moved up or down by the slider 17 with the drive motor 18 to adjust the vertical position of the stage 16 in such a manner as to maintain the inspecting surface at a constant level. By this mechanism, despite existence of stepped portions or undulations on the inspecting surface, the laser beam which is reflected and diffracted on the inspecting surface is invariably directed toward the photo-detector member 8.

Further, by processing the reflected image of the scanning laser light, which is picked up by the TV camera 5, minute surface irregularities as well as locations and sizes of cracks can be detected along with the height of the inspecting surface. In this instance, a picture image of different magnifications in X- and Y-directions can be obtained by employing, for the lens system of the TV camera 5, a couple of cylinder lenses which are located in predetermined spaced positions and in perpendicularly intersecting relationship, instead of employing an ordinary optical lens. For example, in a case where the magnification in X-direction is ten times higher than that of Y-direction, the accuracy of detecting surface irregularities of the specimen can be enhanced by ten times.

The information which is obtained at the image processing unit 6 with regard to the minute surface irregularities and the locations and sizes of cracks on the inspecting surface is sent to the data processing unit 9 to supplement the results of analysis of reflected and diffracted light in judging the nature of the detected surface flaws and defects as will be described hereinbelow.

As described hereinbefore, the laser light reflected and diffracted on the inspecting surface of the specimen 11, which is maintained at a predetermined height, shows diffractions in various directions depending upon the surface condition (existence of flaws, defects, cracks or stains) of the specimen In case of a sound surface free of flaws or other defects, light is reflected rearward at an angle equal to the angle of incidence, and converged and focused on the center measuring point of the photo-detector member 8 located at the point of convergence.

It has been empirically known that there is close relationship between the surface condition (e.g., flaws, defects, stains etc ) of the specimen and the diffraction pattern, and that light diffraction appears in the radial direction at the point of convergence in a certain degree depending upon the size and nature of the flaw or the like. Therefore, the nature of a flaw can be estimated by measuring the distribution of diffracted light, namely, by knowing the direction and the degree of expansion of diffracted light.

Shown at A to D in FIG. 3 are typical diffraction patterns as observed when the laser light is spotted on the surface of a specimen, in which the center of each frame coincides with the point of convergence. In a case where the inspecting surface is a sound smooth surface, no diffraction pattern appears as shown in FIG. 3A. On the other hand, when there is a flaw or defect, a particular diffraction pattern appears depending upon the nature, direction, width and depth of the flaw or defect FIGS. 3B to 3D show diffraction patterns of a stain, a scratched flaw, and a depressed dimple-like flaw, respectively.

The light receiving ends 13a of the optical fiber filaments 13, which are arranged on a concentric circle around the point of convergence, is suitable for measuring the expansion of the diffraction pattern efficiently within a short period of time. The circularly arranged light receiving ends 13a are especially suitable for the measurement of diffraction patterns as diffracted light tends to spread radially from the point of convergence in a particular (angular) direction or directions depending upon the nature of the flaw, and, for the purpose of comparison, the diffracted light which attenuates in proportion to the distance from the point convergence should preferably be measured at equidistant positions from the point of convergence.

Figure 3A:
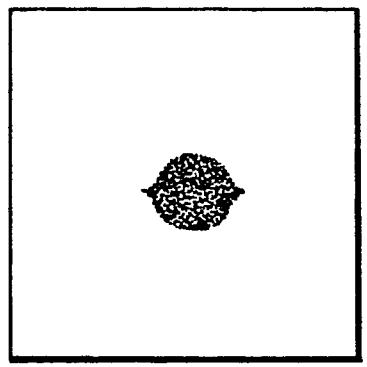
FIGS. 3A-3D is a diagrammatic view of diffraction patterns of various defects.
Figure 3B:
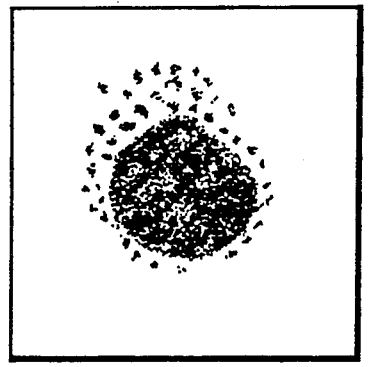
Figure 3C:
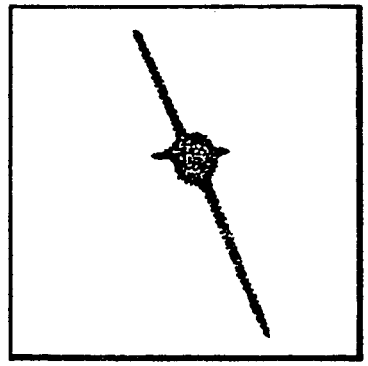
Figure 3D:
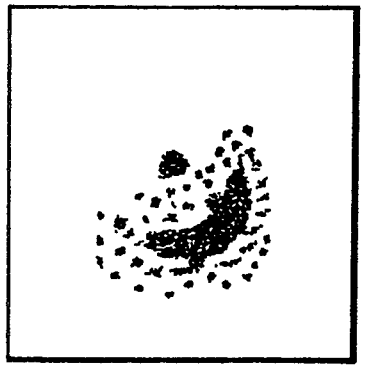
Figure 4:
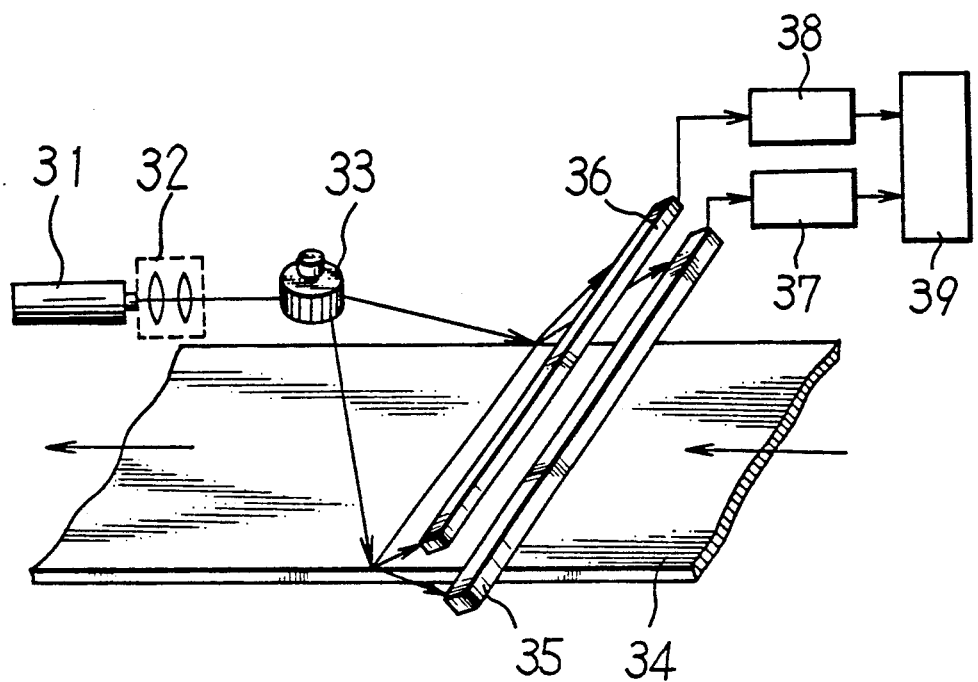
FIGS. 4 and 5 are illustrations explanatory of conventional counterparts.
Figure 5:
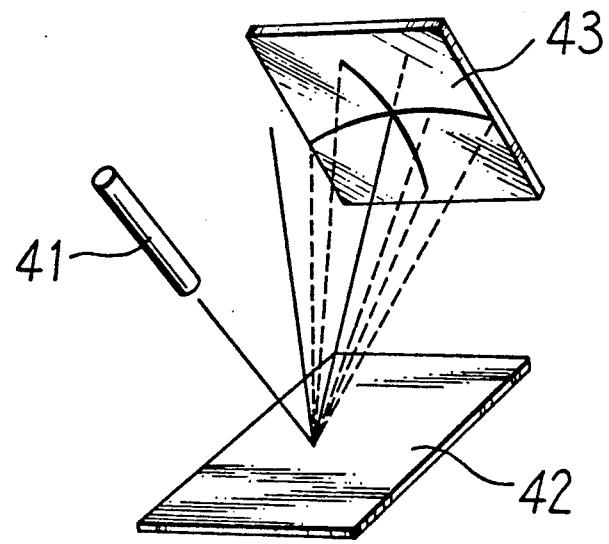

For example, when a diffraction pattern as shown in FIG. 3B or 3C is formed by existence of a surface flaw and received by twelve optical fiber filaments 13 having the respective light receiving ends 13a arranged at angular intervals of 15°, the output of the photo-detector member 8 contains twelve pieces of data. Upon scanning these data two-dimensionally, bright portions indicative of a flaw appear in the picture images in a position corresponding to the flaw. Namely, in case of FIG. 3B, bright portions appear randomly in the picture images of No. 1 to No. 7, and in all of the picture images of No. 8 to No. 12. In case of FIG. 3C, a bright portion appears only in the picture image of No. 11. No changes occur to the picture images in case of FIG. 3A where the inspecting surface is free of flaws.

Accordingly, the nature of a flaw can be known from the distribution of diffracted light energy on the light receiving surface where the direction of diffracted light is detected by directionally corresponding ones of the light receiving ends 13a which are arranged along a circle around the point of convergence.

There is no particular restrictions on the radius of the circle along which the light receiving ends 13a are to be arranged. When the radius is small, it becomes possible to detect diffracted light of feeble energy levels and to reduce the number of the photoelectric transducers although the accuracy of directional (angular) detection becomes lower. On the other hand, when the radius is large, higher accuracy in directional detection can be guaranteed to facilitate discrimination of the nature of defects, but it becomes necessary to provide a larger number of photoelectric transducers of high sensitivity.

From an optical point of view, it is known that diffraction generally appear in a symmetrical form having a center at the point of convergence (direct reflection). Therefore, it suffices to locate the optical fiber filaments 13 along a concentric circle on the light receiving surface of the photometric member 8 along only a right or left half of the circle as shown in FIG. 2.

In this embodiment, the measuring points on the light receiving surface 12 are connected to the photoelectric transducers 14 through the optical fiber filaments 13. This is because, in a case where photomultipliers are employed as the photoelectric transducers for the purpose of accurately detecting diffracted light of feeble energy levels, it is necessary to guide the diffracted light to detecting portions of the photomultipliers which dimensionally difficult to fit in the light receiving surface, and to permit location of the light receiving surface in an arbitrary position. Accordingly, the positions and areas of measuring points can be freely altered by changing the diameter and number of the optical fiber filaments.

During inspection, the slider 19 which holds the specimen 11 is moved in X-direction successively in a predetermined pitch for light-scanning the entire surface of the specimen which needs inspection of surface conditions. At this time, the inspector makes an ultimate judgement as to whether or not the surface condition is acceptable based on an overall assessment of the results of inspection indicated on the display. More particularly, on the part of the apparatus, the picture image taken by the TV camera is sent to the data processing unit 9 along with the results of analysis of the diffraction pattern to determine locations, sizes and nature of surface flaws, defects or cracks if any, indicating the results of analysis on the display 10 or other output device preferably in color graphics showing the nature of defects by colors. Therefore, the inspector can easily recognize the nature of defects from the indicated color distribution in making a judgement of qualification or disqualification.

The picture image taken by the TV camera is used in the manner as follows. The laser spot scanning by the vibrating mirror is synchronized with the video signal of the TV camera, so that the inspecting surface in the detected picture image comes out as a dark surface with bright linear stripes of the laser beam as in the fashion of slit light projection by the light chopping method. Since the angle of incidence of the laser beam and the TV camera position are known beforehand, the height of the inspecting surface scanned by the laser beam can be determined by calculations based on the principle of triangulation using the laser beam portion of the detected picture image.

One of the merits of using the TV camera picture image is that it gives information on the three-dimensional shape of the inspecting surface as described hereinbefore, permitting to move the stage 16 up and down to maintain the scanning position of the laser beam at a constant height.

Another merit is that the stripes in the TV camera picture image discontinue at cracks or similar surface irregularities, helping detection of cracks which cannot be detected by the light diffraction method. Surface irregularities can also be detected from distortion or deformation of the stripes. The sizes of cracks can be determined by counting the number of picture elements in the discontinued portions of the stripes.

The reflected light might fail to enter the photometric detection system in case of a flaw or defect in a deep position or in case of a crack, making the measurement infeasible. Even in such a case, it is possible to obtain information on the geometrical shape of the unmeasurable portion from the picture image taken by the TV camera.

What is claimed is:

1. A method for inspection of surface conditions by scanning a surface area of a specimen with a spot-like light beam projected obliquely from a light source and detecting various defects on the surface of said specimen on the basis of optical data of diffracted light from said specimen surface, characterized in that said method comprises:

detecting the height of said inspecting surface from a reflection position of the scanning light spot picked up by a TV camera located above said inspecting surface;

controlling the vertical position of said specimen according to the output of the height detection in such a manner as to maintain said inspecting surface of said specimen at a constant height;

converging reflected and diffracted light from said inspecting surface by means of a parabolic cylinder mirror toward a photo-detector having measuring points at the point of convergence of said mirror and in a number of positions on and along a concentric circle around said point of convergence;

measuring the energy of reflected and diffracted light by photoelectric transducers connected to said measuring points; and displaying display data corresponding to data received by the TV camera and the photoelectric transducers on a display, thereby displaying locations, sizes and nature of surface flaws, defects and stains of said specimen.

2. A method according to claim 1, further comprising the step of:

processing the data received by the TV camera and photoelectric transducer into said display data.

3. An apparatus for inspection of surface conditions, essentially comprising in combination:

a laser generator for projecting a laser beam for irradiation;

a vibrating mirror adapted to change the direction of irradiation of the laser beam at high speed for scanning the laser beam in a direction perpendicular to a direction of transfer of a surface of a specimen under inspection;

a first parabolic cylinder mirror for converting the scanning light from the vibrating mirror into a parallel light beam and projecting the same obliquely on the surface of said specimen;

a TV camera located above said surface of a specimen under inspection;

an image processing unit for detecting the height of said surface of a specimen under inspection through analysis of the picture image picked up by said TV camera;

a second parabolic cylinder mirror for converging the scanning laser light scattered from said surface of a specimen under inspection;

a photo-detector adapted to receive reflected and diffracted light from said parabolic cylinder mirror at a number of measuring points located at the point of convergence of said second mirror and on and along a concentric circle around said point of convergence and to measure the energy level of the incident reflected and diffracted light by means of photoelectric transducers;

a specimen mounting stage arranged to be controlled by the output of said image processing unit to maintain said inspecting surface of said specimen at a constant height;

a slider for moving the stage in the direction of transfer of said specimen;

a data processing unit adapted to judge locations, sizes and nature of surface flaws, defects and cracks, if any, according to information from said image processing unit and photo-detector; and a display for indicating the results of judgement of said data processing section.

4. An apparatus for inspection of surface conditions as defined in claim 3, wherein light receiving ends of optical fiber filaments are located at said measuring points on said light receiving surface of said photodetector to receive diffracted light from said parabolic cylinder mirror, ends of the fibers opposite the light receiving ends being connected to photoelectric transducers.

5. An apparatus for inspection of surface conditions as defined in claim 3 or claim 4, wherein said light receiving ends of said optical fiber are located on said light receiving surface of said photo-detector only along a bisected segment of a concentric circle around said point of convergence.

6. An apparatus for inspection of surface conditions as defined in claim 3, wherein said TV camera includes in a lens system thereof a couple of cylindrical lenses located in predetermined spaced positions and in perpendicularly intersecting relationship with each other.

7. A method for inspection of surface conditions by scanning a surface area of a specimen with a spot-like light beam projected obliquely from a light source and detecting various defects on the surface of said specimen on the basis of optical data of diffracted light from said specimen surface, characterized in that said method comprises:

detecting the height of said inspecting surface from a reflecting position of the scanning light spot picked up by a TV camera located above said inspecting surface;

controlling the vertical position of said specimen according to the output of the height detection in such a manner as to maintain said inspecting surface of said specimen at a constant height;

converging reflected and diffracted light from said inspecting surface by means of a parabolic cylinder mirror toward a photo-detector having measuring points at the point of convergence of said mirror and in a number of positions on and along a concentric circle around said point of convergence;

measuring the energy of reflected and diffracted light by photoelectric transducers connected to said measuring points; and displaying locations, sizes and nature of surface flaws, defects and stains of said specimen on a display with combined processing of two information, one of which is an image information obtained by the TV camera as to variations in surface level and cracks or the like on said inspecting surface and the other one is obtained by said photoelectric transducers.

* * * * *